US011202799B2

(12) United States Patent
Nivoliez (10) Patent No.: US 11,202,799 B2
(45) Date of Patent: Dec. 21, 2021

(54) USE OF THIOSULFATE TO POTENTIATE THE ANTI-PATHOGENIC EFFECT OF LACTOBACILLI

(71) Applicant: PROBIONOV, Arpajon-sur-Cere (FR)

(72) Inventor: Adrien Nivoliez, Yolet (FR)

(73) Assignee: PROBIONOV, Arpajon-sur-Cere (FR)

( * ) Notice: Subject to any disclaimer, the term of this patent is extended or adjusted under 35 U.S.C. 154(b) by 158 days.

(21) Appl. No.: 15/899,273

(22) Filed: Feb. 19, 2018

(65) Prior Publication Data

US 2018/0360874 A1 Dec. 20, 2018

Related U.S. Application Data

(63) Continuation of application No. 14/413,660, filed as application No. PCT/EP2013/064451 on Jul. 9, 2013, now abandoned.

(30) Foreign Application Priority Data

Jul. 9, 2012 (FR) ...................................... 1256570

(51) Int. Cl.

| A61K 35/747 | (2015.01) |
|---|---|
| A61K 33/04 | (2006.01) |
| A61K 9/00 | (2006.01) |
| A61K 9/14 | (2006.01) |
| A61K 9/19 | (2006.01) |
| A61K 45/06 | (2006.01) |
| A61K 47/02 | (2006.01) |

(52) U.S. Cl.
CPC ............ *A61K 33/04* (2013.01); *A61K 9/0034* (2013.01); *A61K 9/143* (2013.01); *A61K 9/19* (2013.01); *A61K 35/747* (2013.01); *A61K 45/06* (2013.01); *A61K 47/02* (2013.01)

(58) Field of Classification Search
CPC ...... A61K 33/04; A61K 9/0034; A61K 9/143; A61K 9/19; A61K 45/06; A61K 47/02; A61K 35/747; A61K 9/0053; A61K 9/14; A61K 9/48; A61P 31/10; A61P 31/02; A61P 15/02; A61P 13/02; A61P 13/00; A61P 31/04

See application file for complete search history.

(56) References Cited

U.S. PATENT DOCUMENTS

| 6,093,394 | A | 7/2000 | Chrisope |
| 6,468,526 | B2 | 10/2002 | Chrisope |
| 6,919,172 | B2 | 7/2005 | Depablo et al. |
| 7,807,440 | B2 | 10/2010 | Molin et al. |
| 2002/0044926 | A1 | 4/2002 | Reid et al. |
| 2010/0151026 | A1 | 6/2010 | Liu et al. |
| 2010/0310713 | A1 | 12/2010 | Viebke et al. |
| 2011/0008467 | A1 | 1/2011 | Sherman et al. |

FOREIGN PATENT DOCUMENTS

| CA | 2176474 A1 | 6/1995 |
| CN | 101919917 A | 12/2010 |
| EP | 1911455 A1 | 4/2008 |
| FR | 1426226 A | 1/1966 |
| WO | 8404675 A1 | 12/1984 |
| WO | 0035465 A2 | 6/2000 |
| WO | 2006045475 A1 | 5/2006 |
| WO | 2010004005 A1 | 1/2010 |
| WO | 2010133314 A1 | 11/2010 |
| WO | 2011066949 A1 | 6/2011 |

OTHER PUBLICATIONS

Vuyst, L. DE; "Nutritional factors affecting nisin production by *Lactococcus lactis* subsp. *lactis* NIZO 22186 in a synthetic medium;" Journal of Applied Bacteriology, XP008163829, vol. 78, No. 1, Jan. 1, 1995; pp. 28-33.
Karthikeyan, V, et al. "Isolation and partial characterization of bacteriocin produced from Lactobacillus plantarum;" African Journal of Microbiology Research, XP055073122, vol. 3, No. 5, May 1, 2009; pp. 233-239.
Nivoliez, Adrien, et al.; "Influence of manufacturing process on in vitro properties of the probiotic strain Lactobacillus rhamnosus Lcr35;" Jounral of Biotechnology, Aug. 31, 2012, 160(3-4), e-published Apr. 2012; 6 pages.
Maria Silvina Juarez Tomas, et al.; "Estimation of combined effects of carbon and nitrogen sources on the growth and bacteriocin productiton of Lactobacillus salivarius from human source;" Journal of Basic Microbiology, XP055073125, vol. 50, No. 2, Jan. 15, 2010; pp. 190-199.
St. Amant, Diane C.; et al.; "Inhibition of Neisseria gonorrhoeae by *Lactobacillus* species that are commonly isolated from the female genital tract;" Infection and Immunity, XP-002692927, vol. 70, No. 12, Dec. 2002; pp. 7169-7171.
Internet publication "Trophigil", XP-002692926, retrieved from internet address: http://web.archive.org/web/20120807162456/http://www.eurekasante.fr/medicaments/vidal-famille/medicament-btropg01-TROPHIGI . . . , May 22, 2012; 3 pages.
Korchemkin A M; "Treatment with hyposulfite of gonorrhea resistant to sulfanilamides;" Database Medline—U.S. National Library of Medicine (NLM), Bethesda, MD, XP-002692925, Vestnik Venerologii I Dermatologii, No. 2, 1946, 1 page.
Database Abstract—Thomson Scientific, London GB, Week 201128, XP002692924, and CN 101 919 917 (Zhang, B.; et al.), Dec. 22, 2010; 7 pages.

(Continued)

*Primary Examiner* — Lynn Y Fan
(74) *Attorney, Agent, or Firm* — McBee Moore & Vanik IP, LLC (57) ABSTRACT

The present invention relates to the use of thiosulfate to potentiate the anti-pathogenic effect of lactobacilli bacteria, the thiosulfate being in a quantity of at least 100 mg for $10^7$ to $10^{10}$ CFU of lactobacilli. The invention also relates to a pharmaceutical composition including at least 100 mg of thiosulfate per gram, in combination with a *Lactobacillus crispatus* strain, and to its use in the treatment of urogenital infections such as vaginosis, candidosis and urinary tract infections.

6 Claims, 8 Drawing Sheets

(56) References Cited

OTHER PUBLICATIONS

Database Abstract—"Decay-prevention microbicide for use in cosmetics, pharmaceuticals and foodstuffs, contains 1,2-octane diol and thiosulfite, disulfite, sulfite or hydrogen sulfite;" Thomson Scientific, London, GB, Week 200563, XP-002692928, and JP 2005 232014 (Mandom KK), Sep. 2, 2005; 10 pages.

Probios. Probios dispersible powder microbial products. Probios. 2011; 1-3.

Menard J. Antibacterial treatment of bacterial vaginosis: current and emerging therapies. International Journal of Women's Health. 2011;3:295-305.

Kiefer D. Warding off chronic yeast and bacterial infections. Life Extension Magazine. 2008;1-6.

Sghir et al. Continuous culture selection of bifidobacteria and lactobacilli from human faecal samples using fructooligosaccharide as selective substrate. Journal of Applied Microbiology. 1998;85:769-777.

**Figure 1 : Counts of Lcr35® and *C. albicans* in co-culture (n=2) over time**

Figure 6

USE OF THIOSULFATE TO POTENTIATE THE ANTI-PATHOGENIC EFFECT OF LACTOBACILLI

CROSS-REFERENCE TO RELATED APPLICATIONS

This application is a Continuation of U.S. patent application Ser. No. 14/413,660, filed 8 Jan. 2015, which is a National Stage entry of International Application No. PCT/EP2013/064451, filed 9 Jul. 2013, which claims priority to French Patent Application No. 1256570, filed 9 Jul. 2012. The disclosures of the priority applications are incorporated in their entirety herein by reference.

FIELD OF THE INVENTION

The present invention relates to compositions including lactobacilli in combination with thiosulfate, the thiosulfate potentiating the anti-pathogenic effect of said lactobacilli.

In a healthy woman, the urogenital flora comprises nearly 50 different species of microorganisms. Among these microorganisms, 95% of the population is composed of various strains of lactobacilli, also called "Döderlein's bacillus". These lactobacilli help protect against pathogens by various mechanisms, including production of hydrogen peroxide, lactic acid and bacteriocins, inhibition of adhesion and spreading of pathogens. In particular, these lactobacilli maintain an acidic pH by producing lactic acid from the glycogen present in the vaginal mucus. Thus, the growth of numerous pathogens of the vaginal flora, such as *Gardnerella vaginalis, Prevotella bivia, Neisseria gonorrhoeae, Mycoplasma, Mobiluncus* and, above all, *Candida albicans*, is inhibited.

The normal vaginal flora is thus principally composed of lactobacilli forming a protective biofilm on the surface of the mucous membrane. The lactobacilli most commonly identified in the vagina are notably *Lactobacillus crispatus, Lactobacillus jensenii, Lactobacillus vaginalis, Lactobacillus inners* and *Lactobacillus gasseri*.

Vulvovaginal candidiasis affects 70-75% of women at least once during their reproductive years, and about 40-50% will have a second episode. The incidence of recurrent vulvovaginal candidiasis (defined as at least 4 episodes per year, including 2 confirmed by mycological examination) has been estimated at 5-8%. This benign ailment has a very negative impact on patients' quality of life and generates significant healthcare expenditures. Such pathology is difficult to treat because of the multifactorial pathogenesis of this affection.

The traditional maintenance therapy using an oral or vaginal antifungal must last at least 6 months, but the relapse rate remains high with 60-70% of women having a recurrence in the two months following discontinuation of the treatment. Moreover, antifungals have frequent side effects and their long-term use can promote an occurrence of bacterial vaginosis.

Bacterial vaginosis is due to a qualitative and quantitative imbalance of the normal vaginal flora which can lead to the virtually complete disappearance of lactobacilli, to the benefit of anaerobic flora, and also to the emergence of bacteria such as *Gardnerella vaginalis* and *Atopobium vaginae*. Bacterial vaginosis is one of the most frequent vaginal infections with a frequency rate of 10 to 15. This benign pathology in women can be serious during pregnancy as it can cause premature deliveries, low birth-weights and spontaneous abortions.

Bacterial vaginosis and other imbalances of the vaginal microflora are commonly treated by antibiotic therapy. This treatment has the typical disadvantages of antibiotic treatments and is proving to be less and less effective. Furthermore, it aims to eliminate the pathogenic flora but also destroys the normal beneficial flora.

STATE OF THE ART

The oral or vaginal administration of 'beneficial' lactobacilli has been described to promote vaginal health. In particular, the patent applications WO 84/04675, WO 2000/035465, US 2002/0044926 and WO 2006/045475 describe the oral or vaginal administration of lactic bacteria to promote vaginal health and to prevent recurrences of vulvovaginal candidiasis.

The patent application WO 2010/004005 reports the administration of prebiotics combined with a plant extract containing isoflavones, to promote the development of a normal vaginal flora.

The preferred lactobacilli are *Lactobacillus rhamnosus, Lactobacillus crispatus* and *Lactobacillus vaginalis*. The U.S. Pat. Nos. 6,093,394, 6,468,526 and 7,807,440, as well as the patent application US 2010/0151026, describe the administration of specific *Lactobacillus crispatus* strains.

These lactobacilli can be administered in lyophilized form or in solution, and optionally in combination with other active agents. Indeed, although lactobacilli have a real and recognized anti-pathogenic effect, it is often insufficient for them to be able to fight an infection. Additional active agents, or agents that potentiate the anti-pathogenic effect of lactobacilli, are actively sought by the scientific community.

It has been proposed to administer lactobacilli in combination with an antimicrobial agent, the bacterium being microencapsulated (EP 0 732 916 B1); in the presence of lactic acid and an extract of garlic (EP 1 911 455 A1); in the presence of gum arabic (EP 2 211 640 A1); in the presence of estrogens and/or gestagens (WO 2010/133314); or in the presence of an antibiotic and an unsaturated, esterified fatty acid (WO 2011/066949).

The results presented in the article by Nivoliez et al. (2012) indicate that the processes used to manufacture probiotic bacteria can play an important role in the characteristics of lactobacilli prepared industrially.

Sodium thiosulfate is used as an excipient in numerous pharmaceutical and veterinary compositions containing lactobacilli, such as the compositions TROPHIGIL, PROBIOS® and ALLBIO®. Furthermore, the patent application CN 20091145852 describes a drug composed of extracts of Chinese plants and sodium thiosulfate. This drug is proposed notably for the treatment of gonorrhea.

In these compositions, sodium thiosulfate is used as an excipient, and not as an active agent.

Only the American patent application US 2011/0008467 describes pharmaceutical compositions including solely pharmaceutical grade sodium thiosulfate. The therapeutic applications proposed are as follows: treatment of cyanide or platinum poisoning, vascular calcification and dermatological diseases.

SUMMARY OF THE INVENTION

The anti-pathogenic effect of lactobacilli genuinely exists but is not sufficiently strong in most cases to fight infection (see FIG. 2A), and it is thus often necessary to use in addition other active ingredients such as antibiotics or antifungals.

The present invention proposes a means of potentiating the anti-pathogenic effect of lactobacilli. The inventors have indeed discovered that the combination of thiosulfate, notably sodium thiosulfate, and lactobacilli makes it possible to potentiate the anti-pathogenic effect of these lactobacilli, when the thiosulfate is present at a concentration of at least 100 mg/gram of powder, for a powder including from $10^7$ to $10^{10}$ CFU/g of lactobacilli.

This "anti-pathogenic" effect is characterized in particular by an inhibition of the growth of vaginal pathogens such as *Gardnerella vaginalis*, *Prevotella bivia*, and especially *Candida albicans*.

The invention also relates to a pharmaceutical composition including at least 100 mg/g of sodium thiosulfate in combination with *Lactobacillus crispatus*.

DETAILED DESCRIPTION OF THE INVENTION

The present invention relates to the use of thiosulfate to potentiate the anti-pathogenic effect of *Lactobacillus* bacteria, the thiosulfate being in a quantity of at least 100 mg/gram of powder, for a powder including from $10^7$ to $10^{10}$ CFU/g of lactobacilli.

Definitions

The term "potentiate" means to give a greater effectiveness, to increase the beneficial effects of an active ingredient. In particular, the potentiating agent (here, thiosulfate) does not itself act against pathogens, but acts via lactobacilli whose anti-pathogenic effect it potentiates.

The term "anti-pathogenic effect" refers to the preventive and curative action of lactobacilli with respect to the various pathogens whose growth can be inhibited by the presence of lactobacilli. This effect is expressed via various mechanisms: lowering of pH, production of hydrogen peroxide ($H_2O_2$), production of lactic acid and/or acetic acid, production and secretion of bacteriocins, peptides, organic acids and short-chain fatty acids, and inhibition of the adhesion and expansion of pathogens. In particular, this anti-pathogenic effect is measured as the rate of inhibition of pathogen growth, and as the rate of production of bacteriocins and peptide compounds having antimicrobial properties.

The term "pathogens" refers to all pathogens likely to settle in the urogenital tract, and in particular *Gardnerella vaginalis*, *Prevotella bivia*, *Neisseria gonorrhoeae*, *Mycoplasma*, *Mobiluncus*, *Candida albicans* and *Candida glabrata*, as well as to pathogens likely to cause enteric infections, such as, for example, Enterobacteriaceae, including *Escherichia coli*, *Salmonella*, *Staphylococcus*, *Clostridium difficile* and *Shigella*.

The term "lactobacilli" refers to all bacteria of the genus *Lactobacillus*, immotile, facultatively anaerobic, Gram-positive bacteria of variable shapes and sizes. Most lactobacilli convert lactose and other simple sugars into lactic acid. Lactobacilli colonize the vagina and gastrointestinal tract and are an important component of the endogenous intestinal and vaginal flora.

The present invention principally relates to lactobacilli constituting the vaginal flora; it is understood, however, that the invention can be carried out with other types of lactobacilli such as those present in the gastrointestinal tract (in particular *Lactobacillus acidophilus*, *Lactobacillus reuteri*, *Lactobacillus salivarius*, *Lactobacillus gasseri*, *Lactobacillus casei* and *Lactobacillus rhamnosus*).

The term "colony forming unit" or "CFU" refers to the unit of measure generally recognized by persons skilled in the art for quantifying bacteria capable of founding a colony.

The term "thiosulfate" refers to thiosulfate ions ($S_2O_3^{2-}$). This is the basic form of thiosulfuric acid ($H_2S_2O_3$), unstable in an aqueous medium.

According to a preferred aspect of the invention, the pathogens whose growth is inhibited by the combination of thiosulfate and lactobacilli belong to the family of *Candida albicans*, *Prevotella bivia*, *Gardnerella vaginalis*, *Mycoplasma* or *Mobiluncus*.

*Candida albicans* is the most important and well-known yeast species of the genus *Candida*. It causes fungal infections (candidiasis or candidosis) mainly of the mucous membranes of the digestive tract and female reproductive system.

*Prevotella bivia* is an anaerobic bacterium, which mainly causes vaginosis and urinary tract infections.

*Gardnerella vaginalis* is a bacterium with a pleomorphic rod or coccobacillus shape. It is frequently found in cases of vaginosis (nonspecific vaginitis), either as the only pathogenic bacterium or in combination with other bacteria. It produces a perforating toxin that only affects human cells. It can also be encountered in the blood, urine and pharynx.

*Mycoplasma* is a family of more than 100 species of bacteria that are insensitive to families of antibiotics such as penicillin or beta-lactams. In particular, *Mycoplasma genitalium* is responsible for genital infections (urethritis, cervicitis, vaginitis, salpingitis) and sterility problems.

*Mobiluncus* is an anaerobic Gram-positive bacterium often found associated with *Gardnerella vaginalis* in bacterial vaginosis.

The term "vaginosis" refers to an imbalance of the vagina's microbial flora. It is characterized by the disappearance of lactobacilli and the multiplication of anaerobic bacteria such as *Gardnerella vaginalis*.

The term "candidiasis" refers to a fungal infection caused by yeasts of the genus *Candida*. *Candida albicans*, the most common species, is part of the usual flora of the oropharynx and digestive track and can also be present in a small quantity in the normal vaginal flora. Vulvovaginal candidiasis is quite common and can be prone to several recurrences.

The term "urinary infection" refers to colonization of the urine by bacteria, most often expressed as symptoms of urinary infection. The bacteria most commonly concerned are *Escherichia coli* (75% of cases), *Proteus mirabilis* and *Klebsiella*, all three Enterobacteriaceae (Gram-negative bacilli).

According to the invention, neither vaginosis nor candidiasis nor urinary tract infections can be regarded as sexually-transmitted infections such as gonorrhea.

According to an aspect of the invention, the thiosulfate is selected from sodium thiosulfate or potassium thiosulfate. Preferentially, sodium thiosulfate is used. Sodium thiosulfate consists of sodium ions and thiosulfate ions. Preferably, the quantity used is at least 100 mg/g of powder, preferentially at least 150 mg, and more preferentially at least 200 mg of thiosulfate per gram of powder, this powder including between $10^7$ and $10^{10}$ lactobacilli bacteria (CFU). Preferentially, the quantity of sodium thiosulfate in the final product will be approximately 230 mg/gram of powder including $10^7$ to $10^{10}$ CFU of lactobacilli.

According to a preferred aspect of the invention, the thiosulfate is used in a quantity of about 230 mg/gram of powder, for a powder including between $10^8$ and $10^{10}$ CFU of lactobacilli per gram, and more preferentially between $10^9$ and $10^{10}$ CFU/gram. Persons skilled in the art, specialists in lyophilization, will be able to adapt the quantity of thiosulfate added before lyophilization to obtain the quantity desired in the powder obtained after lyophilization. In particular, this final quantity of sodium thiosulfate is obtained by adding 113 g/liter of sodium thiosulfate to the bacterial culture medium, before lyophilization. The examples show, however, that a simple addition of 1 g/liter of thiosulfate in the bacterial culture medium makes it possible to potentiate the effects of lactobacilli in culture.

According to a preferred aspect of the invention, the lactobacilli are *Lactobacillus rhamnosus* and/or *Lactobacillus crispatus*. The preferred strains are notably the strain Lcr35® and the strain BLL2005.

The invention also relates to a pharmaceutical composition including at least 100 mg of thiosulfate, preferentially at least 150 mg, and more preferentially at least 200 mg of thiosulfate per gram of powder, in combination with a *Lactobacillus crispatus* strain. According to a preferred embodiment, the quantity of lactobacilli per gram of composition will be between $10^7$ and $10^{10}$ CFU, more preferentially between $10^8$ and $10^9$ CFU/g.

Preferably, the *Lactobacillus crispatus* strain is in lyophilized form. The strain can be the only lyophilized element of the composition, but preferably the strain is lyophilized in a medium including additional constituents, which will be added before or after the lyophilization step. In particular, the sodium thiosulfate can be added before lyophilization, notably in a quantity of 113 g/liter of bacterial culture medium. The sodium thiosulfate can also be added in a quantity of 1 g/liter, 5 g/liter, 10 g/liter, 20 g/liter, 30 g/liter, 50 g/liter or 100 g/liter of bacterial culture medium.

According to another particular aspect of the invention, the pharmaceutical composition further includes a preservation matrix and/or excipients well-known to persons skilled in the art, and optionally other active ingredients having a complementary action.

In particular, this composition can include the following active ingredients: hormones (estriol, progesterone, etc.), anti-inflammatory agents and/or bactericidal agents and/or antifungal agents. Persons skilled in the art will be able to determine which active ingredients can advantageously be combined with a *Lactobacillus crispatus* strain. This composition also includes, according to a specific aspect of the invention, several lactobacilli strains.

The invention also relates to a pharmaceutical composition including the culture supernatant of a *Lactobacillus* strain, preferentially *Lactobacillus crispatus*, cultivated in the presence of thiosulfate, in particular sodium thiosulfate, in particular at least 100 g/liter of sodium thiosulfate in the culture medium. This culture supernatant contains thiosulfate but does not contain lactobacilli. It has a strong anti-pathogenic activity.

As shown in the examples, the presence of thiosulfate potentiates the secretion of bacteriocins, peptide compounds having antimicrobial properties. It is thus likely that the "culture supernatant" no longer containing lactobacilli contains large amounts of bacteriocins, secreted beforehand by the lactobacilli.

These pharmaceutical compositions are formulated for vaginal administration or oral administration. In particular, the dosage forms used will be capsules, tablets, creams, liquid or oily suspensions, or any other suitable medical device.

The invention also relates to a pharmaceutical composition including at least 100 mg, preferentially at least 150 mg, and more preferentially at least 200 mg of thiosulfate per gram of powder, in combination with a *Lactobacillus crispatus* strain, for its use in the treatment of urogenital infections such as vaginosis, candidosis and urinary tract infections.

Preferentially, this composition will include about 230 mg of sodium thiosulfate in combination with $10^8$ to $10^9$ CFU/g of a *Lactobacillus crispatus* strain.

The optimal modes of administration, dosing schedules and dosage forms of the compounds and compositions according to the invention can be determined according to the criteria generally taken into account in the establishment of a pharmaceutical treatment suited to a patient, such as, for example, the patient's age or weight, the gravity of the patient's general state, the tolerance for the treatment and the side effects observed. Urogenital infections will preferably be treated by the administration of one or two 350 mg capsules per day.

The present invention also relates to a pharmaceutical composition including at least 100 mg, preferentially at least 150 mg, and more preferentially at least 200 mg of thiosulfate per gram of powder, in combination with $10^7$ to $10^{10}$ CFU of a *Lactobacillus* strain, for its use in the treatment of urogenital infections such as vaginosis, candidosis and urinary tract infections, by potentiation of the anti-pathogenic effect of lactobacilli.

Lastly, the invention also relates to a novel use of thiosulfate, and in particular sodium thiosulfate, for the treatment of urogenital infections such as vaginosis, candidiasis and urinary tract infections, by potentiation of the anti-pathogenic effect of lactobacilli.

The thiosulfate can be used in combination with lactobacilli, as described above, or administered alone for the purpose of potentiating the anti-pathogenic effect of lactobacilli present endogenously in the vaginal cavity.

DESCRIPTION OF THE FIGURES

FIG. 2. Compositions including various lactobacilli strains without (FIG. 2A) or with (FIG. 2B) sodium thiosulfate, for the inhibition of pathogenic *C. albicans*. The results are expressed as the decimal logarithmic ($\log_{10}$) reduction of the number of CFU between the count at T0 and at the various sampling points (T=4 h, 24 h and 28 h).

FIG. 3. Composition including the strain *L. crispatus* BLL2005 without (FIG. 3A) or with (FIG. 3B) sodium thiosulfate, for the inhibition of various pathogens. The results are expressed as the decimal logarithmic ($\log_{10}$) reduction of the number of CFU between the count at T0 and at the various sampling points (T4h, T24h and T28h).

EXAMPLES

Example 1—Combination of the Strain *L. Crispatus* BLL2005 and Various Concentrations of Sodium Thiosulfate, for the Inhibition of Pathogenic *C. albicans*

Co-incubation tests were carried out between the pathogenic strain *Candida albicans* UMIP48.72 (ATCC10231) and the strain *L. crispatus* BLL2005, formulated with various concentrations of sodium thiosulfate. The base formulation corresponds to Formulation A (see below) in which the sodium thiosulfate concentration was varied. This element is added at the conclusion of fermentation, before the lyophilization step.

Formulation A includes the following constituents:
 Culture medium: 116 g/l milk, 15 g/l dextrose, 10 g/l autolyzed yeast, 2 ml/l Tween
 Lyophilization medium: 110 g/l milk, 101.5 g/l FOS, 9.5 ml/l glutamate, 5.25 g/l ascorbic acid, 113 g/l sodium thiosulfate The following formulations were tested (table 1):

| Batch number | Formulation A combined with a sodium thiosulfate concentration of: |
|---|---|
| E289-2005 | 0 g/l |
| E290-2005 | 10 g/l |
| E291-2005 | 25 g/l |
| E292-2005 | 50 g/l |
| E293-2005 | 75 g/l |
| E115-2005 = Formulation A | 113 g/l |

Description of the Protocol:
Culture Media Used:
 Lactobacilli strains: MRS broth/agar (at 37° C.).
 Pathogenic strains: Sabouraud broth and agar (at 25° C.).
 Test culture medium: homogeneous mixture of the two culture media.
Preparation of Inocula:
 Work with samples without cold blocking.
 Probiotic product: 0.2 g is placed in 20 ml of MRS broth—in an incubator at 37° C. for 48 hours.
 Pathogenic strain: 0.2 ml is place in 20 ml of Sabouraud broth at 25° C. for 48 hours.
 The purity of the strains is verified by isolation.
Preparation of controls:
 For the manufacture of the pathogenic control, 5 ml of inoculated Sabouraud broth (titer near $1.10^8$ CFU/ml) is placed with 5 ml of non-inoculated MRS broth.
 For the manufacture of the probiotic control, 5 ml of inoculated MRS (titer near $1.10^8$ CFU/ml) is placed with 5 ml of non-inoculated Sabouraud broth.
Placing the Inocula in Contact:
 Place 5 ml of the pathogenic strain with 5 ml of the probiotic strain. Samples are taken directly in the mixture.
Measurements:
 Counting of the pathogen and the probiotic at $T_0$, $T_4$, $T_{24}$ and $T_{28h}$
 Determination of the pH of the solution at $T_0$, $T_4$, $T_{24}$ and $T_{28h}$
Results:
 The results are presented in FIG. 1 and in table 2 below. The results are expressed as the decimal logarithmic ($\log_{10}$) reduction of the number of CFU between the count at T0 and at the various sampling points (T4h, T24h and T28h).

Figure 1:
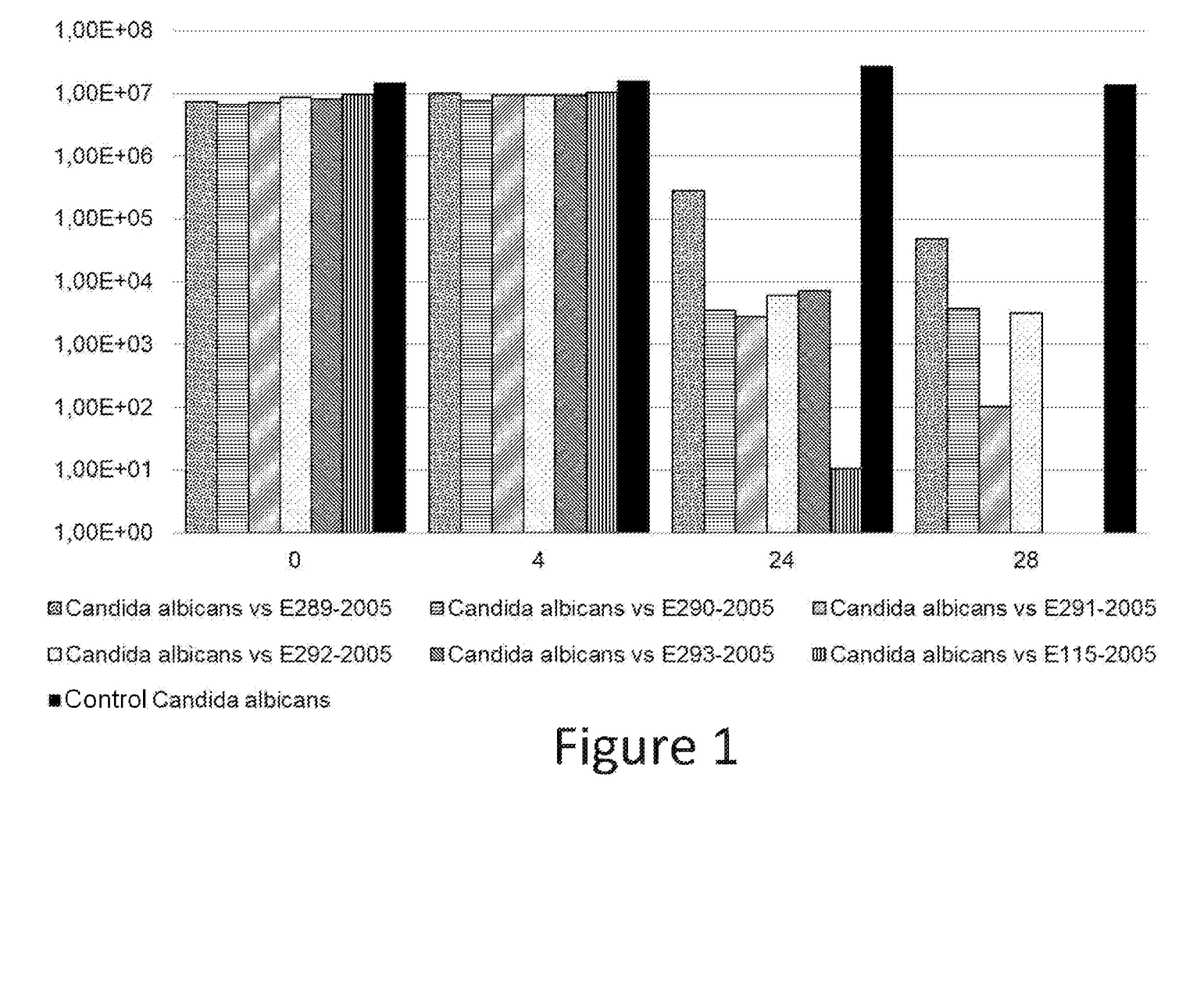
FIG. 1. Influence of sodium thiosulfate concentration in the formulation of the strain *L. crispatus* BLL2005 on inhibition of pathogenic *C. albicans*. The results are expressed as the decimal logarithmic ($\log_{10}$) reduction of the number of CFU between the count at T0 and at the various sampling points (T=4 h, 24 h and 28 h).

| | Reduction in $\log_{10}$ | | |
|---|---|---|---|
| | 4 h | 24 h | 28 h |
| *Candida albicans* vs E289-2005 (0 g/l) | 0 | 1 | 2 |
| *Candida albicans* vs E290-2005 (10 g/l) | 0 | 3 | 3 |
| *Candida albicans* vs E291-2005 (25 g/l) | 0 | 3 | 5 |
| *Candida albicans* vs E292-2005 (50 g/l) | 0 | 3 | 3 |
| *Candida albicans* vs E293-2005 (75 g/l) | 0 | 3 | 7 Complete inhibition |
| *Candida albicans* vs E115-2005 (113 g/l) | 0 | 6 | 7 Complete inhibition |

For all tests, counts of the strain BLL2005 remained constant during co-incubation.
Conclusion:
 This experiment makes it possible to show that from 10 g/l of sodium thiosulfate in Formulation A of the strain *L. crispatus* BLL2005, we observe after 28 hours of co-incubation an increase in inhibition against the pathogenic *Candida albicans* strain tested of at least 1 log. From a concentration of 75 g/l, a complete inhibition of the pathogen is obtained in vitro.

Example 2—Combination of Various *Lactobacillus* Strains and Sodium Thiosulfate, for the Inhibition of Pathogenic *C. albicans*

Strains Tested:
 The following strains were tested with or without 'Formulation A' including 113 g/liter of sodium thiosulfate (table 3):

| PB 0003 | CIP 69.17 | *Lb jensenii* T |
| PB 0004 | CIP 101887 | *Lb reuteri* T |
| PB 0033 | CIP 105932 | *Lb vaginalis* T |
| PB 0041 | BLL2005 | *Lb crispatus* |
| PB 0039 | Lcr35 | *Lb casei* variety *rhamnosus* |

Figure 2A:
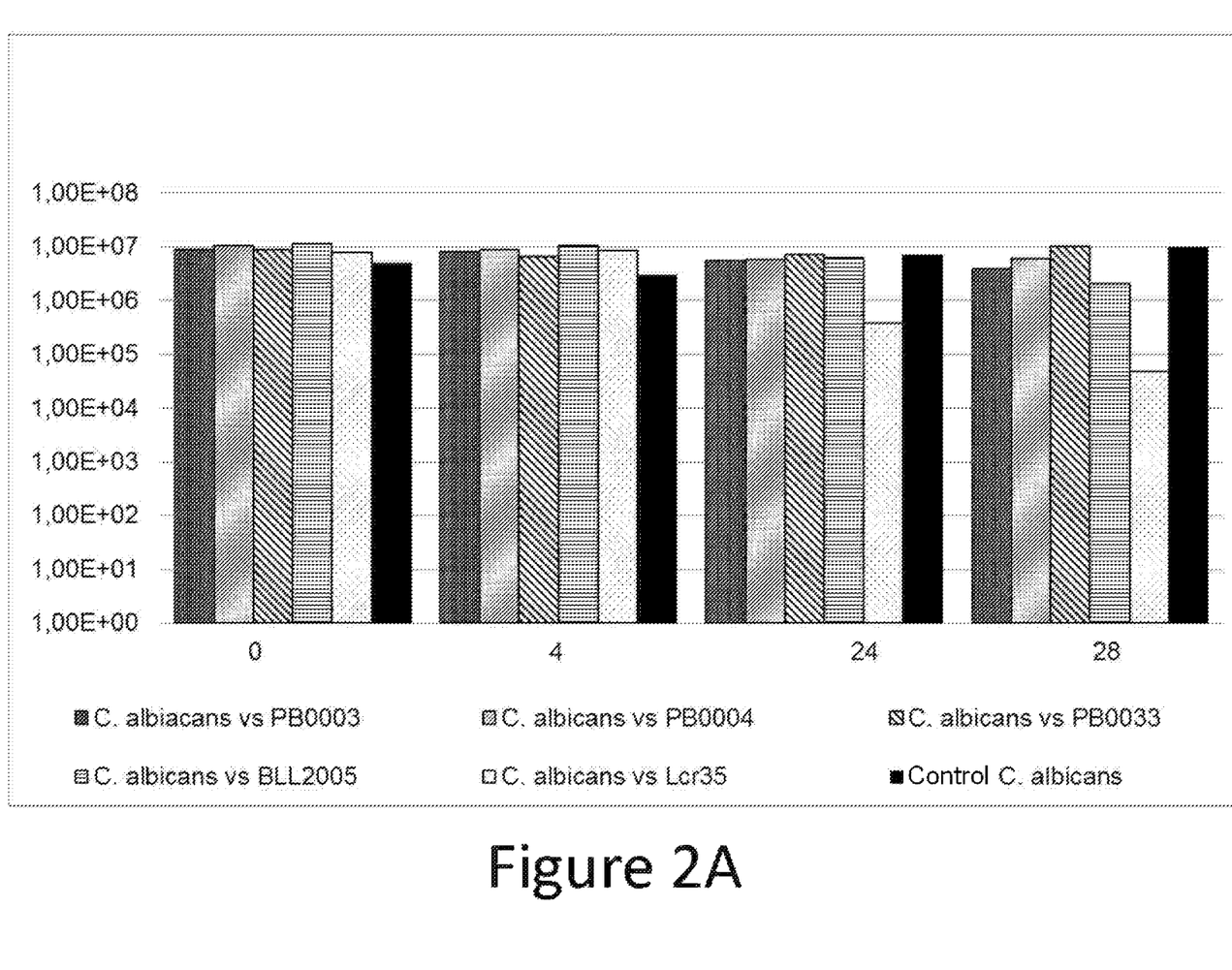
Figure 2B:
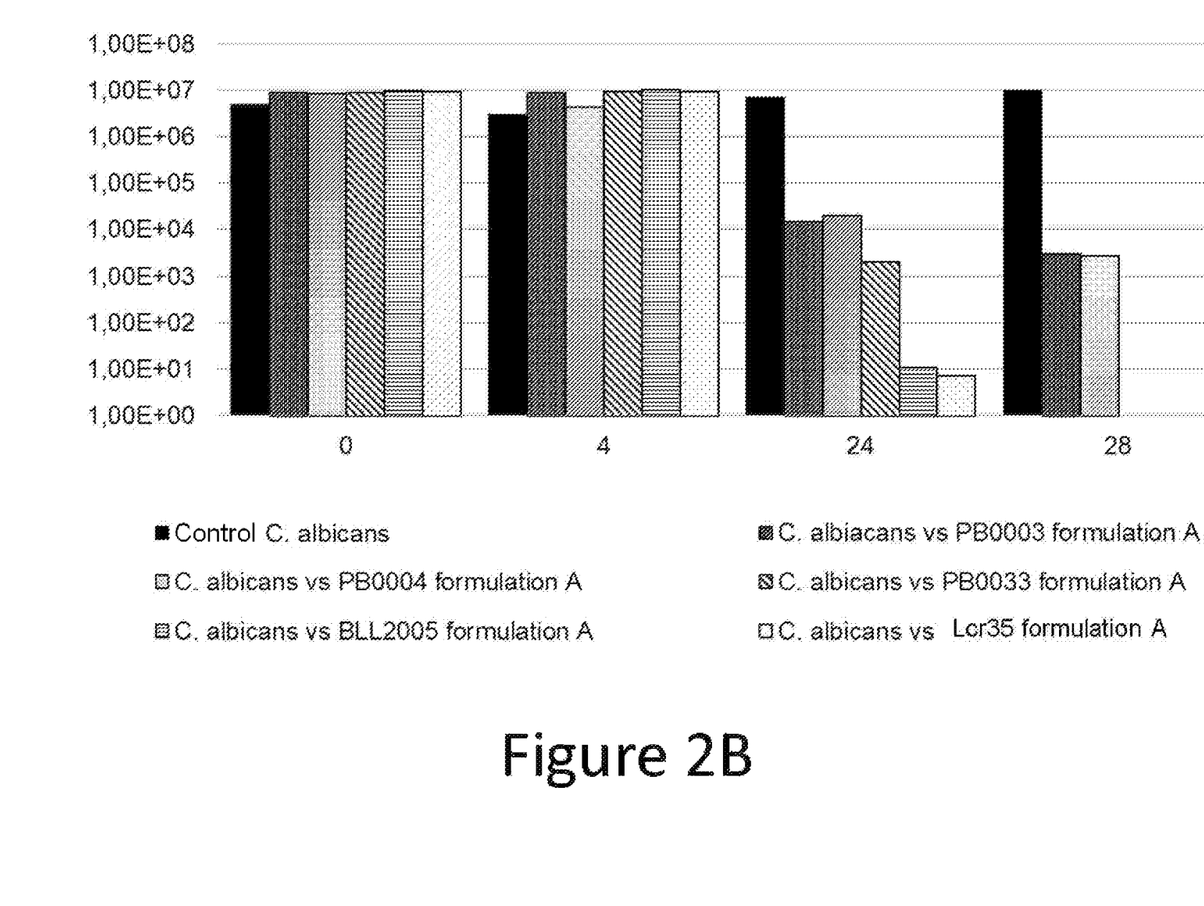

The protocol is equivalent to that described in example 1.
For all tests, counts of the lactobacilli strains remained constant during co-incubation.
The results are shown in FIG. 2. The results are expressed as the decimal logarithmic ($\log_{10}$) reduction of the number of CFU between the count at T0 and at the various sampling points (T4h, T24h and T28h).
Conclusion:
 In their natural state, all of the *Lactobacillus* strains tested have little or no ability to inhibit pathogenic *C. albicans* (see FIG. 2A).
 On the contrary, when Formulation A is used in combination with the strains PB00033, BLL2005 and Lcr35, a complete inhibition of the pathogen after 28 hours of co-incubation is observed. The combination of Formulation A with the strains PB0003 and PB0004 makes it possible to obtain an inhibition of the pathogen of greater than 3 log.
 Thus, the formulation of the various species of lactobacilli with sodium thiosulfate makes it possible for the 5 strains tested to very significantly increase their ability to inhibit pathogenic *Candida albicans*.

Figure 3A:
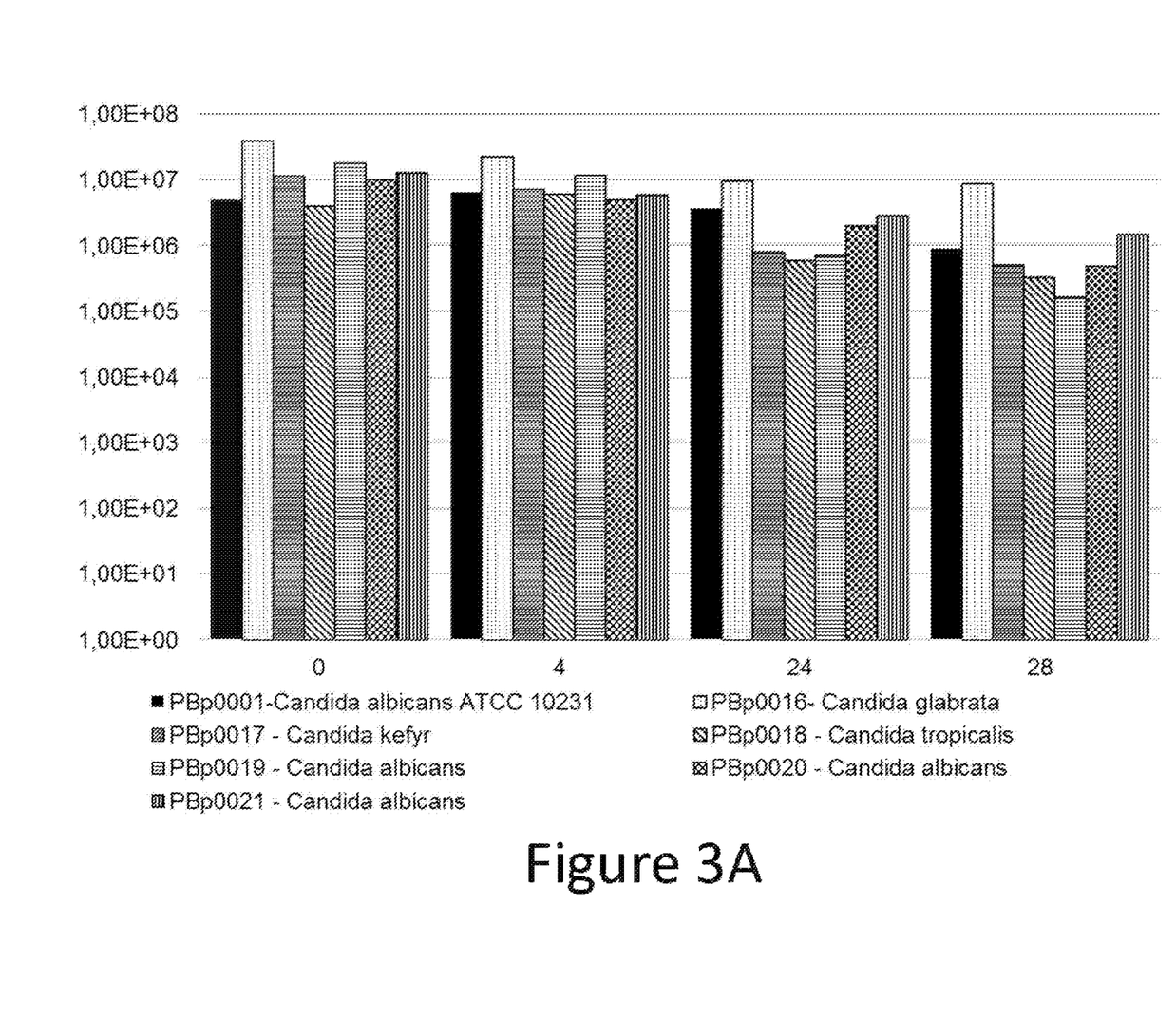
Figure 3B:
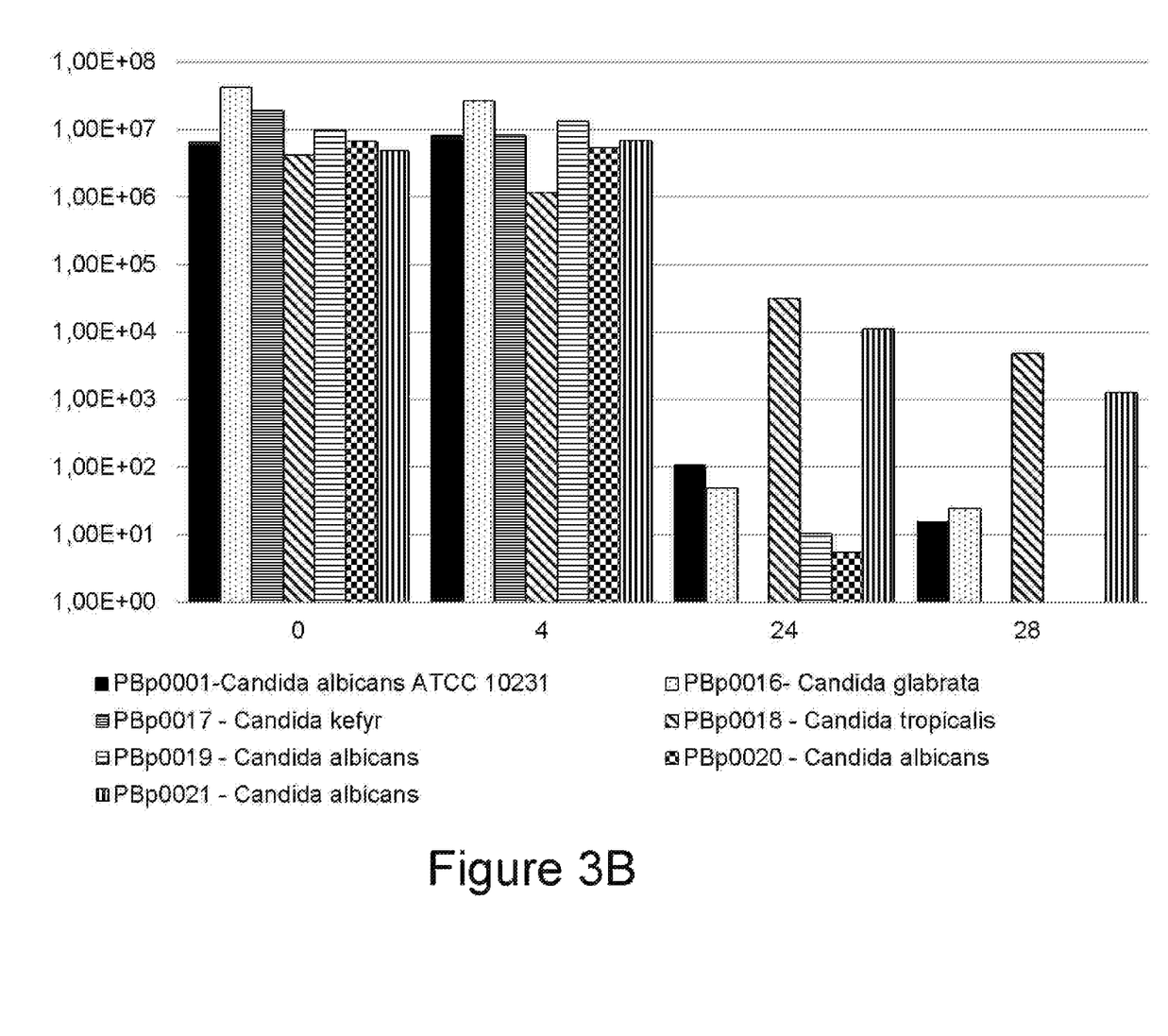

Example 3—Combination of *L. crispatus* BLL2005 and Sodium Thiosulfate, for the Inhibition of Several Pathogens Various co-incubation tests were carried out between various *Candida* strains and the strain *L. crispatus* BLL2005 formulated without sodium thiosulfate (FIG. 3A) or according to Formulation A (FIG. 3B).

TABLE 4

| Pathogenic strains tested: | |
| --- | --- |
| PBp0001 -*Candida albicans* | ATCC 10231 |
| PBp0016 -*Candida glabrata* | clinical isolation |
| PBp0017 -*Candida kefyr* | clinical isolation |
| PBp0018 -*Candida tropicalis* | clinical isolation |
| PBp0019 -*Candida albicans* | clinical isolation |
| PBp0020 -*Candida albicans* | clinical isolation |
| PBp0021 -*Candida albicans* | clinical isolation |

The protocol is equivalent to that described in example 1.

For all tests, the count of the lactobacilli strains remains constant during co-incubation. The pathogen and the probiotic are counted at T0, T4h, T24h and T28h. For all tests, the count of the strain BLL2005 remains constant during co-incubation.

The results are presented in FIG. 3. The results are expressed as the decimal logarithmic ($\log_{10}$) reduction of the number of CFU between the count at T0 and at the various sampling points (T4h, T24h and T28h).

Conclusion:

Formulation A of the strain *L. crispatus* BLL2005 (batch tested: E115-2005) makes it possible to obtain after 28 hours of co-incubation an inhibition greater than or equal to 3 log against all *Candida* strains tested.

Example 4—Preparation of "Formulation A"

The strain BLL2005 is cultivated in the following culture medium:

116 g/l milk, 15 g/l dextrose, 10 g/l autolyzed yeast, 2 ml/l Tween.

After inoculation of the culture medium, fermentation is maintained at a temperature of 37° C. by a suitable thermostatically controlled device for 48 to 72 hours. At the conclusion of fermentation, the culture, having reached a count greater than or equal to $10^8$ CFU/ml, is poured into a mixing tank. The culture is shaken rapidly to break the curd and the following lyophilization adjuvants are added: 110 g/l milk, 101.5 g/l FOS, 9.5 ml/l sodium glutamate, 5.25 g/l ascorbic acid, 113 g/l sodium thiosulfate.

Lyophilization is then carried out according to the standard conditions well-known to persons skilled in the art: the bacteria are distributed aseptically on stainless steel trays, frozen quickly at −40° C., and then subjected to a sublimation operation at −22° C. Incubation is then carried out at 37° C.

The product is then crushed and filtered under controlled atmosphere. The powder obtained can advantageously be mixed with 1% of magnesium stearate in order to facilitate the filling of capsules.

The powder thus obtained is distributed in "0" size capsules in an amount of 350 mg of powder per capsule.

Example 5—Anti-Pathogenic Effects of the Culture Supernatant of Formulation A

The following *Candida* strain was tested: PBp0001—*Candida albicans* ATCC 10231.

Culture Media Used:

Lactobacilli strains: MRS broth/agar (at 37° C.).

Pathogenic strains: Sabouraud broth and agar (at 25° C.).

Test culture medium: homogeneous mixture of the two culture media.

Preparation of Inocula:

Work with samples without cold blocking.

Probiotic product:

0.2 g of Formulation A is placed in 20 ml of MRS broth—in an incubator at 37° C. for 48 hours.

Pathogenic strain: 0.2 ml is placed in 20 ml of Sabouraud broth at 25° C. for 48 hours.

The purity of the strains is verified by isolation.

Preparation of Controls:

For the manufacture of the pathogenic control, 5 ml of inoculated Sabouraud broth (titer near $1.10^8$ CFU/ml) is placed with 5 ml of non-inoculated MRS broth.

For the manufacture of the probiotic control, 5 ml of inoculated MRS (titer near $1.10^8$ CFU/ml) is placed with 5 ml of non-inoculated Sabouraud broth.

Placing Inocula in Contact:

Place 5 ml of the pathogenic strain with 5 ml of the culture supernatant of the probiotic strain. The supernatant was obtained by centrifugation at 10,000 rpm for 10 minutes and then 0.22 μm filtration. Samples are taken directly in the mixture.

Results:

The results are expressed in decimal logarithmic ($\log_{10}$) reduction of the number of CFU between the count at T0 and at the various sampling points (T24h, T48h and T72h).

TABLE 5

| | Reduction in $\log_{10}$ | | |
| --- | --- | --- | --- |
| | 24 h | 48 h | 72 h |
| *Candida albicans* vs supernatant Formulation A BLL2005 | 0 | 7 | 7 |
| Control *Candida albicans* | 0 | 0 | 0 |

Conclusion:

After pre-culture for 48 hours on MRS broth, the supernatant of Formulation A, obtained by centrifugation at 10,000 rpm for 10 minutes and then 0.22 μm filtration, makes it possible to lead to the complete inhibition of the pathogenic *C. albicans* strain from 48 hours of co-incubation.

Example 6—Effect of Sodium Thiosulfate Alone on the Growth of Pathogenic *C. albicans*

Description of the Protocol:

Seed the strain 66 hours before the test is performed.

Place the pre-culture in contact with sodium thiosulfate.

Determine the titer at T0h, T24h, T48h, T72h and T96h.

Preparation of the Test:

Pathogenic Strain:

a *Candida albicans*: Sabouraud broth—0.5 ml of the working vial in 50 ml at 25° C. for 48 hours.

Thiosulfate: de Man, Rogusa and Sharpe (MRS) medium+ sodium thiosulfate (TS) at various concentrations is prepared as below:

MRS medium+1 g/l sodium thiosulfate: 0.3 g of TS is placed in 30 ml of broth

MRS medium+3 g/l sodium thiosulfate: 0.1 g of TS is placed in 10 ml of broth

Placing in Contact:

The test culture medium is a homogeneous mixture of the pathogen's culture medium and MRS medium containing sodium thiosulfate.

*Candida albicans*+ MRS medium+TS (1 g/l): 5 ml of inoculated Sabouraud broth is placed with the pathogenic strain and 5 ml of MRS medium+TS (1 g/l).

*Candida albicans*+ MRS medium+TS (3 g/l): 5 ml of inoculated Sabouraud broth is placed with the pathogenic strain and 5 ml of MRS medium+TS (3 g/l).

*Candida* controls: 5 ml of inoculated Sabouraud broth is placed with the pathogenic strain and 5 ml of MRS broth.

Figure 4:
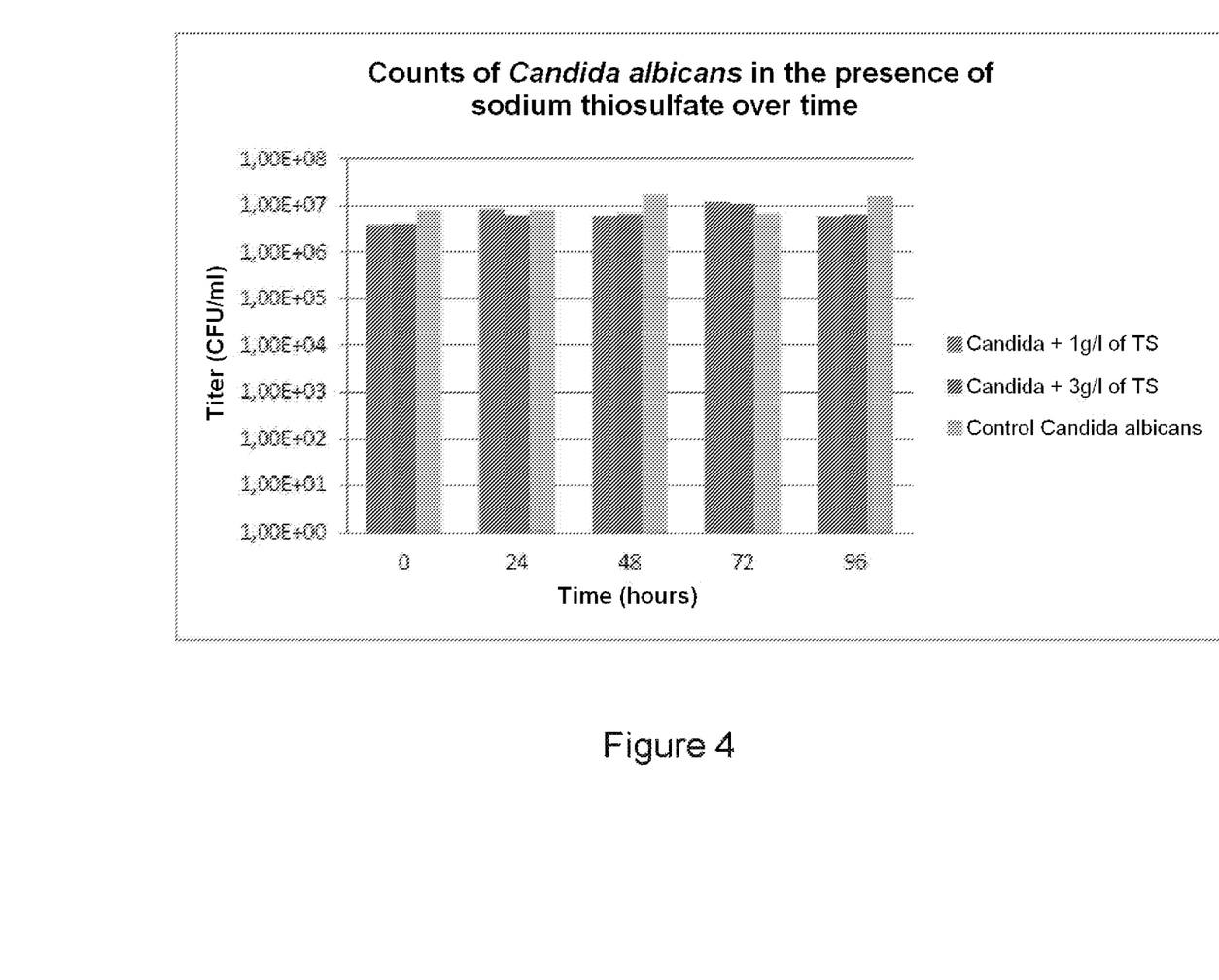
FIG. 4. Effect of sodium thiosulfate alone on the growth of pathogenic *C. albicans*.

The results are presented in FIG. 4.

"Formulation A" including 113 g/liter of sodium thiosulfate was also tested for its action against *Candida*:

Preparation of the *Candida* Control:

For the manufacture of the *Candida* control, 5 ml of inoculated Sabouraud broth is placed with the pathogenic strain (titer near $1 \cdot 10^8$ CFU/ml) and 5 ml of non-inoculated MRS broth.

Samples are taken and titers determined at T0, T4h, T24h and T28h.

TABLE 6

|  | 0 | 4 h | 24 h | 28 h |
|---|---|---|---|---|
| *Candida albicans* vs Formulation A without lactobacilli | 6.00E+06 | 5.50E+06 | 8.00E+06 | 9.00E+06 |
| *Candida* control on Sabouraud | 5.00E+06 | 9.00E+06 | 1.50E+07 | 9.80E+06 |

Figure 5:
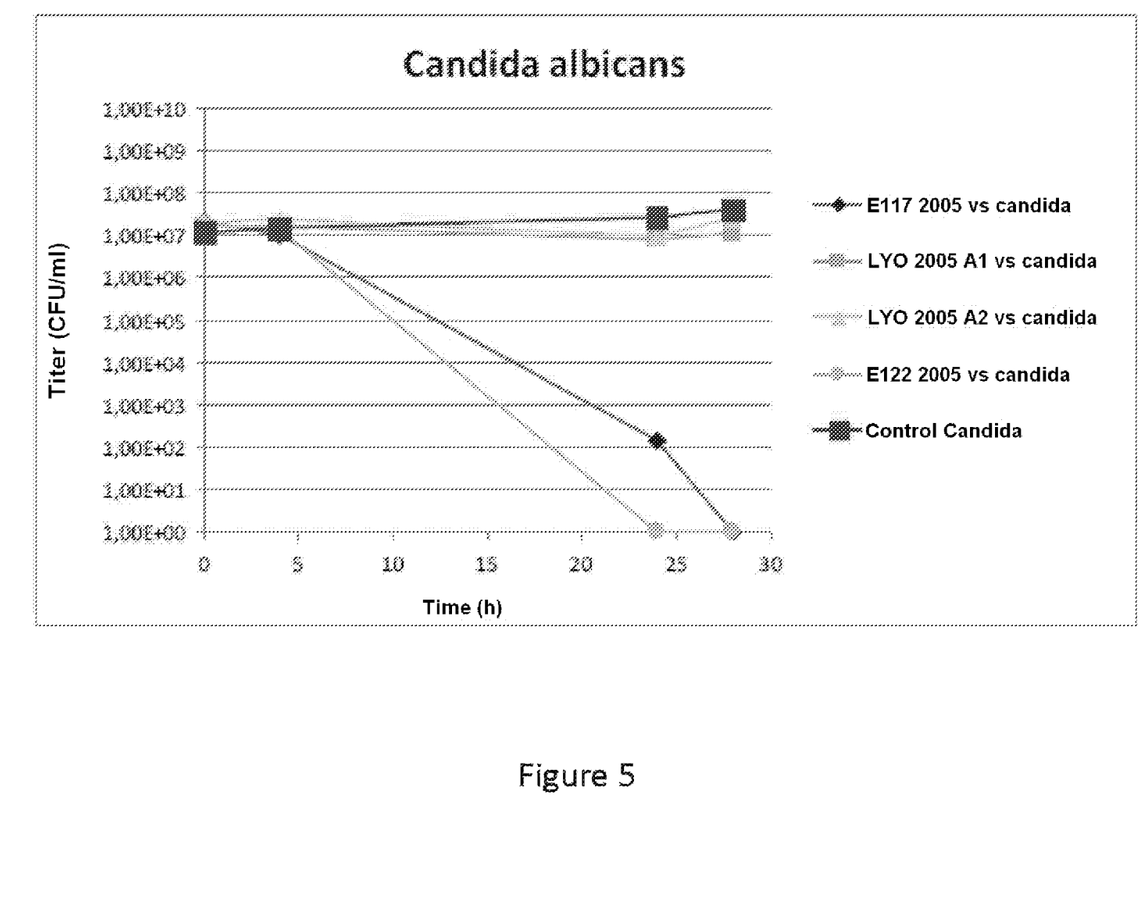
FIG. 5. Effect of 'Formulation A', with or without the presence of *L. crispatus*, on the growth of pathogenic *C. albicans*.

FIG. 5 shows several culture types:

The "*Candida*" control cultivated alone;

Two batches including the strain BLL2005 in Formulation A, as described above;

Two batches including Formulation A alone, without bacteria.

It is apparent that Formulation A, containing 113 g/liter of sodium thiosulfate, has no inhibitory activity on *Candida* growth.

Conclusion:

No antifungal potential is observed in the presence of sodium thiosulfate, regardless of the concentration studied. This experiment shows that thiosulfate itself does not make it possible to inhibit *Candida albicans* growth, and that it acts only as a lactobacilli potentiating agent.

Example 7—Co-Culture of the Strain Lcr35 (*L. rhamnosus*) Formulated with 113 g/Liter of Thiosulfate, and *Candida albicans*, and Production of Bacteriocins by this Strain, with or without Thiosulfate A. Inhibition of *Candida albicans* Growth in the Presence of the Strain Lcr35 (*L. rhamnosus*)

Figure 6:
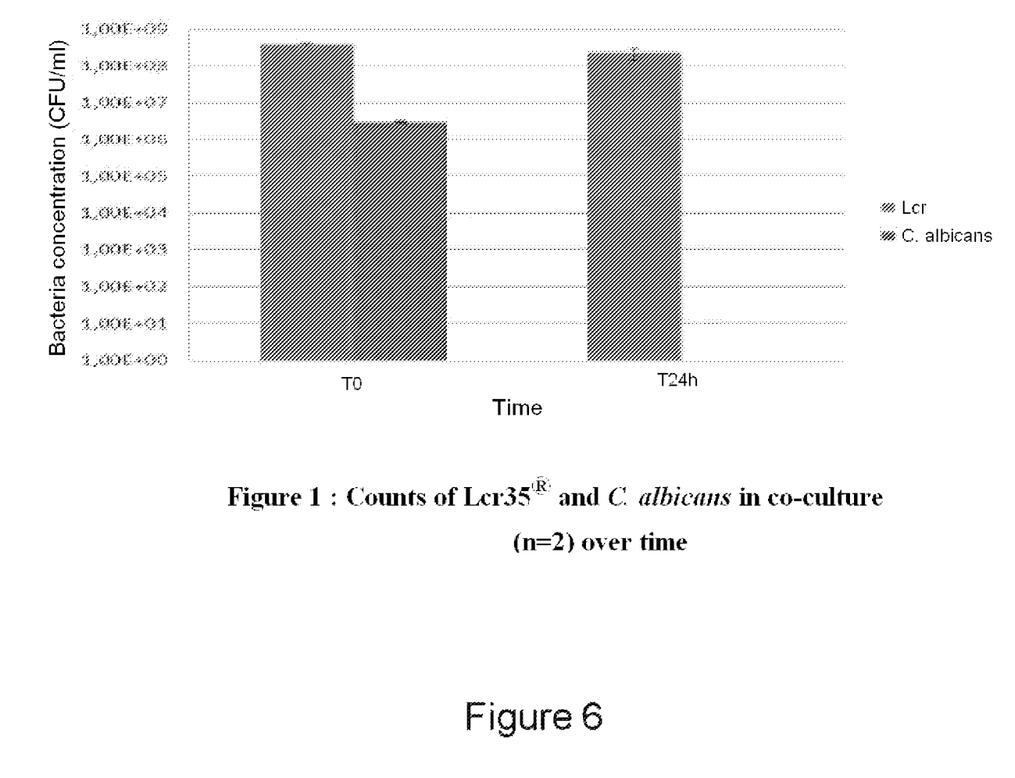
FIG. 6. Co-culture of the strain Lcr35 (*L. rhamnosus*) formulated with 150 mg of thiosulfate (after lyophilization in the final product) and *Candida albicans*.

Counts showed a total inhibition at T24h of the pathogenic strain with a formulation of Lcr35® containing 113 g/l of thiosulfate (FIG. 6).

B. Potentiation of the Expression of Genes Coding for Bacteriocins by Thiosulfate The strain *L. rhamnosus* Lcr35® is able to inhibit the growth of pathogens. Moreover, the strain formulated with thiosulfate is more effective than the strain alone. In order to understand the mechanisms that differ between these two conditions, genes involved in bacteriocin production were sought. In Lcr35®, 7 genes coding for bacteriocins were found.

Materials and Methods

In the literature, various bacteriocins are associated with lactic bacteria. The gene sequences coding for the latter were downloaded from the NCBI (http://www.ncbi.nlm.nih.gov) and then aligned with the genomes of our probiotic strain using BLAST.

Table 7 below presents the various genes coding for bacteriocins found on the genomes of Lcr35®:

| entA | enterocin |
|---|---|
| pedC/papC | pediocin |
| spaR | subtilin |
| cvpA | colicin |
| bac1 | unknown bacteriocin |
| spiA | sakacin |
| lec1 | leucocin |

Detection and Quantification of Genes of Interest

Specific primer pairs for the target genes were previously designed in order to follow their expression by RT-qPCR. Two pure cultures and a co-culture for Lcr35® were prepared, the first with the native probiotic strain, the second with a formulation with 1 g/l of thiosulfate, and the last with a formulation with 113 g/liter of thiosulfate and *C. albicans*.

Results: table 8 below:

| Bacteriocins and coding genes | | Lcr35 | Lcr35 + 1 g/l thiosulfate | Lcr35 + 113 g/l thiosulfate |
|---|---|---|---|---|
| enterocin | entA1 | 1 | 1 | 1 |
|  | entA2 | 1 | 3 | 6 |
| pediocin | papC | 1 | 3 | 5 |
| subtilin | spaR | 1 | 2 | 1 |
| colicin | cvpA | 1 | 3 | 5 |
| unknown bacteriocin | bac1 | 1 | 2 | 2 |
| sakacin | spiA | 1 | 4 | 4 |
| leucocin | lec1 | 1 | 2 | 3 |

The following of the expression of these genes by quantitative RT-PCR showed an overexpression of 6 genes coding for bacteriocins when the strain is formulated with 1 g/l of thiosulfate. When this formulation includes 113 g/l of thiosulfate, 3 genes involved in the secretion of bacteriocins are even more strongly overexpressed. The presence of thiosulfate can thus promote the secretion of bacteriocins which would then participate in the inhibition of pathogens such as *C. albicans*.

We have thus shown that thiosulfate makes it possible to potentiate lactobacilli in the inhibition of pathogenic *Candida albicans*, by enabling notably the overproduction of bacteriocins.

REFERENCES—PATENT DOCUMENTS

WO 84/04675
WO 2000/035465
WO 2006/045475
WO 2010/004005
WO 2010/133314
WO 2011/066949
US 2002/0044926
U.S. Pat. No. 6,093,394
U.S. Pat. No. 6,468,526
U.S. Pat. No. 7,807,440
US 2010/0151026
US 2011/0008467
EP 0 732 916 B1
EP 1 911 455 A1
EP 2 211 640 A1
CN 20091145852

BIBLIOGRAPHICAL REFERENCES

Nivoliez A, Camares O, Paquet-Gachinat M, Barnes S, Forestier C, Veisseire P. "Influence of manufacturing processes on in vitro properties of the probiotic strain *Lactobacillus rhamnosus* Lcr35®." J Biotechnol. 2012 Aug. 31; 160(3-4):236-41. Epub 2012 Apr. 19.

What is claimed:

1. A method for treating a urogenital infection in a patient in need thereof, comprising vaginally administering a composition of lyophilized mixture of *Lactobacillus rhamnosus* Lcr35 and thiosulfate to the patient, wherein the composition comprises from $10^7$ to $10^{10}$ CFU/g of *Lactobacillus rhamnosus* Lcr35 and thiosulfate, wherein the thiosulfate is present in an amount of at least 100 mg/gram of the lyophilized mixture, and wherein the pathogenic organism associated with the urogenital infection is a yeast of the genus *Candida*.

2. The method of claim 1, wherein the thiosulfate is selected from the group consisting of sodium thiosulfate and potassium thiosulfate.

3. The method of claim 1, wherein the composition comprises thiosulfate amounting to about 230 mg/gram of the lyophilized mixture.

4. The method of claim 1, wherein the urogenital infection is selected from the group consisting of candidosis, and urinary tract infection.

5. The method of claim 1, wherein the composition further comprises an agent selected from the group consisting of hormone, anti-inflammatory agent, bactericidal agent, antifungal agent, and a combination thereof.

6. The method of claim 1, wherein the lyophilized mixture comprises fructooligosaccharide (FOS).

* * * * *